United States Patent
Framroze et al.

(10) Patent No.: US 10,827,767 B2
(45) Date of Patent: Nov. 10, 2020

(54) PROCESS TO IMPROVE ENZYME HYDROLYSIS AND RESULTANT PROTEIN FLAVOR AND BIO-ACTIVITY OF FISH OFFCUTS

(71) Applicant: HOFSETH BIOCARE ASA, Ålesund (NO)

(72) Inventors: Bomi Framroze, Ålesund (NO); Roald Rogne, Ålesund (NO)

(73) Assignee: HOFSETH BIOCARE ASA, Ålesund (NO)

( * ) Notice: Subject to any disclaimer, the term of this patent is extended or adjusted under 35 U.S.C. 154(b) by 30 days.

(21) Appl. No.: 16/068,603

(22) PCT Filed: Jan. 6, 2017

(86) PCT No.: PCT/NO2017/050003
§ 371 (c)(1),
(2) Date: Jul. 6, 2018

(87) PCT Pub. No.: WO2017/119820
PCT Pub. Date: Jul. 13, 2017

(65) Prior Publication Data
US 2019/0037882 A1 Feb. 7, 2019

(30) Foreign Application Priority Data
Jan. 6, 2016 (NO) .................................. 20160022

(51) Int. Cl.
| | | |
|---|---|---|
| A23J 3/34 | (2006.01) |
| A23J 1/04 | (2006.01) |
| A23K 10/22 | (2016.01) |
| A23J 1/10 | (2006.01) |
| A23K 20/147 | (2016.01) |
| A23K 50/40 | (2016.01) |
| A23K 50/80 | (2016.01) |
| A23L 33/18 | (2016.01) |
| A23J 1/00 | (2006.01) |
| A61K 8/00 | (2006.01) |
| A23K 10/26 | (2016.01) |
| A61K 8/98 | (2006.01) |
| A61K 35/60 | (2006.01) |

(52) U.S. Cl.
CPC ............. *A23J 3/341* (2013.01); *A23J 1/002* (2013.01); *A23J 1/04* (2013.01); *A23J 1/10* (2013.01); *A23J 3/34* (2013.01); *A23K 10/22* (2016.05); *A23K 10/26* (2016.05); *A23K 20/147* (2016.05); *A23K 50/40* (2016.05); *A23K 50/80* (2016.05); *A23L 33/18* (2016.08); *A61K 8/00* (2013.01); *A61K 8/987* (2013.01); *A61K 35/60* (2013.01); *A23V 2002/00* (2013.01)

(58) Field of Classification Search
CPC ...... A23J 1/002; A23J 1/04; A23J 1/10; A23J 3/34; A23J 3/341; A23K 10/22; A23K 10/26; A23K 20/147; A23K 50/40; A23K 50/80; A23L 33/18; A23V 2002/00; A61K 35/60; A61K 8/00; A61K 8/987
See application file for complete search history.

(56) References Cited

U.S. PATENT DOCUMENTS

| | | | |
|---|---|---|---|
| 159,334 A * | 2/1875 | Kumpf | A47J 43/06 241/27 |
| 3,437,489 A * | 4/1969 | Seiji | A23K 10/22 426/541 |
| 4,288,458 A | 9/1981 | Barnes | |
| 4,350,682 A * | 9/1982 | Balassa | A61K 8/981 424/401 |
| 8,628,817 B2 | 1/2014 | Reid | |
| 2011/0033889 A1* | 2/2011 | Soerensen | A23J 1/10 435/68.1 |
| 2012/0276628 A1* | 11/2012 | Khan | C12M 45/09 435/378 |

FOREIGN PATENT DOCUMENTS

| | | |
|---|---|---|
| CL | 200301447 | 7/2003 |
| CL | 200401642 | 12/2003 |
| CL | 201502058 | 7/2015 |
| CL | 200900292 | 1/2017 |
| CN | 202430226 U | 9/2012 |
| CN | 204861007 U | 12/2015 |
| WO | WO-2005002605 A1 | 1/2005 |
| WO | WO 2014/068601 A1 | 5/2014 |
| WO | WO-2014114767 A1 | 7/2014 |
| WO | WO 2014/207497 A1 | 12/2014 |
| WO | WO 2015/175308 A1 | 11/2015 |

OTHER PUBLICATIONS

Aristotelis T. Himonides et al., "Enzymatic Hydrolysis of Fish Frames Using Pilot Plant Scale Systems", Food and Nutrition Sciences, vol. 2, 2011, pp. 586-593.

(Continued)

*Primary Examiner* — Susan M Hanley
(74) *Attorney, Agent, or Firm* — Morrison & Foerster LLP

(57) ABSTRACT

The present invention relates to the use of turbine mixing during enzymatic hydrolysis of aquatic protein from species such as fish, aquatic mammals, crustaceans and/or mollusks, to obtain high quality aquatic protein hydrolysates, having very low oxidation, improved organoleptic profile and improved biological activity of interest, for human consumption and cosmetics. The turbine mixing can inhibit oxidation during hydrolysis, contribute to an increase in the bio-activity and decrease the bitter taste of the final product. The process can vary in starting material, pre-treatment, type and amount of enzyme, hydrolysis conditions, time, degree of hydrolysis and post-treatment.

24 Claims, 3 Drawing Sheets

(56) References Cited

OTHER PUBLICATIONS

Han B-H et al., "Conditions for Rapid Processing of Modified Fish Sauce using Enzymatic Hydrolysis and Improvement of Product Quality", Journal of the Korean Fisheries Society, vol. 23, No. 2, 1990, pp. 109-124.
Norwegian Search Report issued in Norwegian Application No. 20160022 dated Jun. 6, 2016.
Framroze et al., (2015). "A Comparative Study of the Impact of Dietary Calcium Sources on Serum Calcium and Bone Reformation Using an Ovariectomized Sprague-Dawley Rat Model," J. Nutr. Food Sci., 5(2):1-4.
Slizyte et al., (2005). "Characteristics of protein fractions generated from hydrolysed cod (*Gadus morhua*) by-products," Process Biochemistry, 40:2021-2033.

* cited by examiner

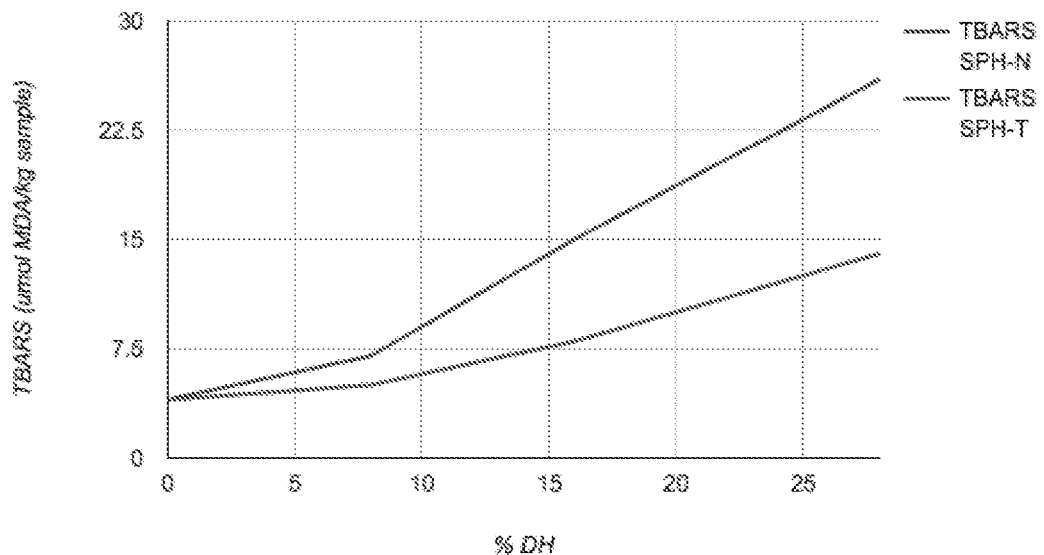

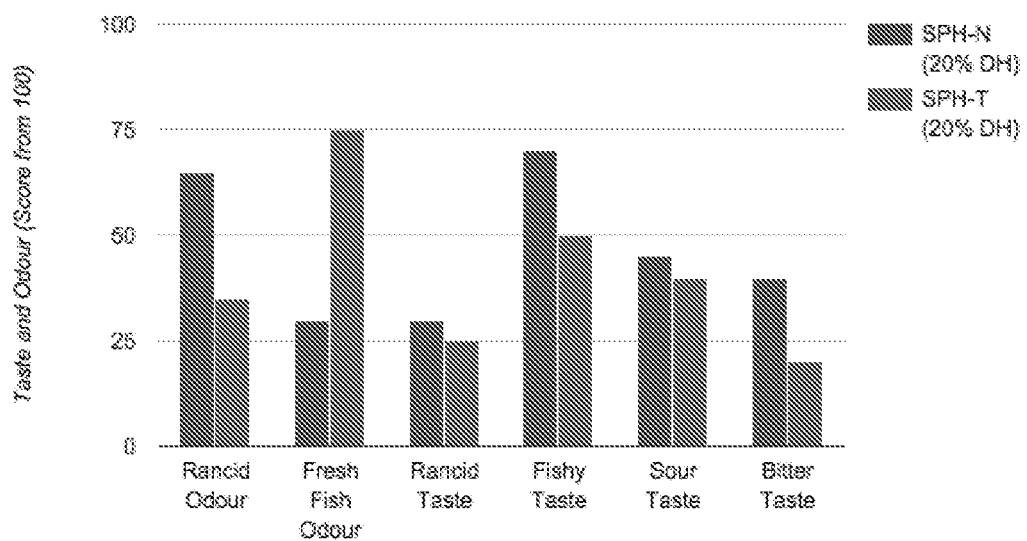

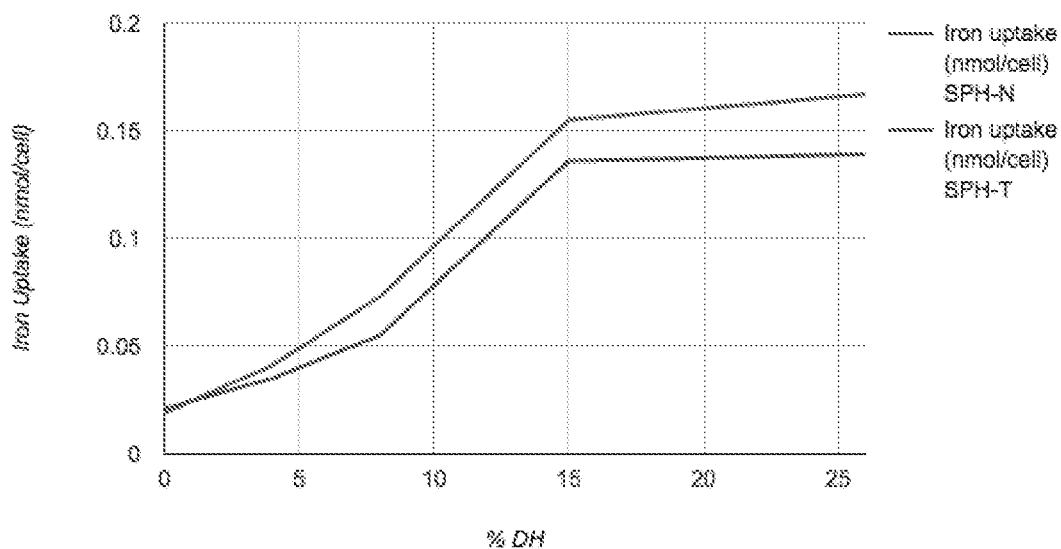

PROCESS TO IMPROVE ENZYME HYDROLYSIS AND RESULTANT PROTEIN FLAVOR AND BIO-ACTIVITY OF FISH OFFCUTS

CROSS-REFERENCE TO RELATED APPLICATION

This application is a 35 U.S.C. § 371 National Phase of PCT Application No. PCT/NO2017/050003 filed Jan. 6, 2017 which claims priority to NO Application No. 20160022 filed Jan. 6, 2016. The disclosure of these prior applications are hereby incorporated by reference herein.

FIELD OF THE INVENTION

The present invention relates to a new method to improve the rate of enzymatic hydrolysis of fish offcuts, aquatic mammals, crustaceans and/or mollusks. More particularly it relates to a turbine mixing system comprising at least one turbine mixer as the agitation component, resulting in much more rapid protein hydrolysis, resulting in a significantly improved taste and odour profile of protein hydrolysate powder which is typically produced from spray drying of the resultant soluble aqueous protein hydrolysate after hydrolysis and resulting in improved bio-activity of the resultant hydrolysate powder.

BACKGROUND OF THE INVENTION

Natural bioactive ingredients have become increasing valuable to consumers and protein hydrolysate powder produced from fish byproducts after filleting is a growing source of nutrition. Particularly in the aquaculture industry, a tremendous amount of utilizable byproduct material is left over after filleting and portioning the fish for direct human consumption. Better utilization of this head, backbone and skin which adds up to 40% of the weight of a gutted salmon will add significant value to the entire seafood industry and reduce the environmental footprint of aquaculture while sharply increasing sustainability. Peptides isolated from various aquatic raw materials have numerous health beneficial bioactivities making them a desirable ingredient in human health foods (Framroze et al., J. Nut. Food Sci. 2015). A major challenge to commercialize these bioactive aquatic protein ingredients of high consistent quality is their very high oxidative instability. Oxidation of the raw material during transport and during processing leads to serious quality deterioration, loss in nutritional value and strong off-odors and flavors. Using enzyme hydrolysis to extract proteins from the over 40% of the fish weight that is discarded as fish byproducts has been identified as a major processing procedure to make better use of our worldwide seafood resources. Several methods and companies produce bioactive fish protein hydrolysates (FPHs), or fish peptides. Although they state that these are suitable for human supplement and nutrition markets, most of these products end up as pet and animal feed. A closer analysis of these products has shown that although the products are of good quality their strong fish taste and odor make their general application into high volume human foods such as powdered drinks and protein bars an impossible task. Methods for producing fish protein hydrolysates of improved quality and more specifically improved desirable organoleptic properties, remains a major inventive goal.

R. Slizyte et al., Process Biochemistry, vol. 40, 2005, pages 2012-2033 have studied how raw material mixtures combined from different separated cod by-products influence the composition of the substrate for hydrolysis. The influence of using an endo-peptidase (Flavourzyme) or exo-petidase (Neutrase) and the amount of added water on yield, nutritional, physiochemical and functional properties of the hydrolysis products has been studied as well. Hydrolysis was performed in a 4 L closed glass vessel stirred with a marine impeller (150 RPM). The enzymatic hydrolysis was started when the temperature of the mixture was 50° C. by adding either 0.1% Flavourzyme 500 L or 0.3% Neutrase 0.8 L. The hydrolysis proceeded for 60 min. No effects on taste and odour were shown.

B.-H. Han et al., Bull. Korean Fish. Soc., vol. 23, no. 2, 1990, pages 109-124 describe a method for manufacturing of a hydrolysate from mackerel waste to be used in the preparation of fish sauce of high quality stability and favourable flavour. The chopped waste was homogenized with water and hydrolysed by commercial proteolytic enzymes such as Complex enzyme-2000 and Alcalase in a cylindrical vessel with 4 baffles and 6-bladded turbine impeller. Optimal pH and temperature for the hydrolysis with Complex enzyme-2000 were 8.0 and 50° C., and those with Alcalase were 9.0 and 55° C. In both cases, the hydrolysing time was 100 minutes. Thermal treatment of the hydrolysate with 6% of invert sugar for 2 hours at 90° C. was adequate to inactivation of the enzymes and pasteurisation of the hydrolysate. Flavour, taste and colour of the hydrolysate were improved during the thermal treatment due to browning reaction products produced because of the addition of invert sugar. The browning reaction products result in antioxidative and bactericidal effects.

SUMMARY OF THE INVENTION

The objective of this invention is to address the problem of oxidation during enzyme hydrolysis of aquatic proteins which leads to unacceptable organoleptic properties and to provide consumers with a high quality consistent aquatic protein hydrolysate powder with positive nutraceutical and health effects.

We have identified that oxidation products arising during enzyme hydrolysis of fish byproducts lead to increased fishy taste and odor and can also have a negative effect on the bio-activity. Furthermore, we have surprisingly identified that the use of turbine mixing during the processing of enzymatically hydrolysed aquatic protein can address this problem sufficiently. The high speed turbine mixing in contrast to normal mixing in a reactor inhibits oxidation during hydrolysis by increasing the rate of hydrolysis by over 3× (three times), reduces the induction of oxygen into solution which accelerates oxidative degradation and contributes to a sufficient improvement in fishy taste and odor so that the powder produced can be directly used in protein drinks and bars made for human consumption. The decreased oxidative degradation result is evidenced with a thiobarbituric acid reactive substance (TBARS) oxidation level test while the improved bio-activity result is evidenced by a CACO-2 cell iron uptake test as shown in the accompanying examples and figures herein.

We have further identified that the use of high speed turbine mixing according to this invention and during enzymatic hydrolysis of aquatic proteins can not only inhibit oxidation and improve fishy taste and odor but also decreases the bitter taste of the resultant hydrolysate powder, which is another major problem in human use of protein hydrolysates in general and fish protein hydrolysates in particular. These results were evidenced with a sensory panel test shown in the accompanying examples and figures herein.

Thus the present invention provides a process for producing high quality aquatic protein hydrolysates which process comprises the use of a high speed turbine mixing system during enzymatic hydrolysis. This results in improved hydrolysates with desirable organoleptic properties and enhanced bio-activities. The invention further provides aquatic protein hydrolysates produced with the process of the invention, and products comprising the hydrolysates, and uses thereof. The process, hydrolysate and use thereof are defined in the accompanying claims.

Definitions

As used herein, the terms "turbine mixing", "high speed turbine mixing" and "jet mixing" have the same meaning and can be seen as synonymous terms. The said terms imply the following features and properties:
  Axial flow pattern
  Typical RPM—2000-4000
  Homogenous mixing
  No air entrainment
  No sedimentation
  No floating of product on the surface
  Rapid mixing of entire content
  No baffles/flow deflectors required
  Low shear due to short residence time in the mixing head results in short process time This is in contrast to the terms "normal mixing", "conventional mixing" and "impeller based mixing" which imply the following features and properties:
  Radial flow pattern (rotational flow)
  Max RPM—200
  Non-uniform and incomplete mixing
  Strong aeration, (Results in: Oxidation, change of colour, problems with the heat transfer etc.)
  Sedimentation
  Floating
  Incomplete mixing of the vessel contents
  Dead zones around the area of the baffles
  Local shear forces, long process times

DETAILED DESCRIPTION OF THE INVENTION

The present invention provides a process for producing an aquatic protein hydrolysate with enzyme hydrolysis, comprising the steps of:
  a) subjecting a protein source material, water and an enzyme to turbine mixing to obtain enzymatic hydrolysis of the protein material;
  b) stopping the enzymatic hydrolysis by deactivating the enzyme under turbine mixing; and
  c) separating the obtained hydrolyzed aquatic peptide fraction from solid material.

The protein source material is selected from material from fish, including fish muscle, fish skin, fish viscera, fish bones, fish heads, other fish byproducts, and any combination thereof; aquatic mammals; crustaceans, including whole crustaceans, crustacean meat and crustacean shells and process byproducts; and mollusks.

In a preferred embodiment of the process according to the invention, the process comprises grinding or mincing of the protein source material in the presence of water, and utilizing the minced pulp in the hydrolysis reaction.

The enzyme used is selected from the group consisting of proteases from bacterial, fungal or marine species, which may be a mixture of endo and exo proteases from *Bacillus* strains, Subtilisin, including Subtilisin from *Bacillus licheniformis* such as Alcalase®, Protamex®, Flavourzyme®, Neutrase®, Protease A "Amano", Pescalase®, Fromase™, Promod31™ and Maxatase™.

In a preferred embodiment of the process according to the invention, the turbine mixing takes place in a turbine mixing system incorporated into the reactor from the side or the top and can be fully or partially submerged in the reaction mass.

According to another preferred embodiment of the process, it comprises the steps of:
  adjustment of the protein material prior to the hydrolysis to a protein content in the range of 0.1% to 30% w/v (protein/water);
  adjustment of the said material to a pH in the range of 5 to 9;
  adjustment of the mixture to a convenient temperature at which the selected enzyme(s) does not become heat inactivated, in the range 30 to 80° C.;
  allowing the enzymatic hydrolysis to proceed for a period in the range from about 10 minutes to 1 hour or until the degree of hydrolysis (% DH) has reached a desired value in the range 2 to 70% DH; and
  stopping the enzymatic hydrolysis by deactivating the enzyme.

The stoppage of the enzymatic hydrolysis according to step b) of the present process is carried out by deactivation of the employed enzyme with a stoppage step selected from:
  (i) raising the temperature of the said reaction mixture to a level not below 60° C., for 5 to 60 minutes, followed by cooling, and
  (ii) deactivation of the employed enzyme by altering the pH to pH where said enzyme is deactivated, such as a pH below about 5 or above about 9.

In a preferred embodiment of the process, the hydrolyzed aquatic peptide fraction and solid material obtained in step b) of the process are separated by concentration.

The separation of the protein hydrolysate may be performed by filtration.

In a preferred embodiment of the process, the separation of the protein hydrolysate is performed by filtration using ultra filtration (UF) membranes, preferably with molecular weight cut-off selected from 30, 10, 5, 3 and 1 kDa.

In another preferred embodiment of the process, the separation of the protein hydrolysate is performed by centrifugation at a speed between 500 and 10000 G and elimination of the residue obtained.

That is, recovery of the protein hydrolysate may be performed by concentration.

According to a further embodiment of the process, the obtained hydrolyzed aquatic peptide fraction is subjected to drying.

That is, recovery of the protein hydrolysate may be performed by drying.

According to still a further embodiment of the process, the solid material separated in step c) is dried and sifted to produce bones which have less than 1% w/w protein on the bone surface. Preferably, the dry sifting is carried out using a series of decreasing mesh size vibrating sieves.

According to one embodiment of the process, the degree of hydrolysis is followed or measured in the final product.

In another aspect, the present invention provides an aquatic protein hydrolysate, obtainable by the process defined above.

The said aquatic protein hydrolysate has a reduced TBARS value compared to aquatic protein hydrolysates produced without turbine mixing which result in a protein hydrolysate having an improved organoleptic profile.

The said aquatic protein hydrolysate also has an increased iron uptake profile compared to aquatic protein hydrolysates produced without turbine mixing which result in a protein hydrolysate having an improved bio-activity.

The aquatic protein hydrolysate of the present invention may be in a form selected from a capsule; a dried form, including powder form, flakes, granules, pellets; a liquid; a semi-liquid; a suspension; an emulsion; and a syrup.

Furthermore, the present invention provides use of the protein hydrolysate as produced by the present invention and defined above, in a food product, a food supplement, pet food, animal feed, fish feed, fertilizer, cosmetic products, pharmaceutical preparations, nutraceutical preparations, and medicaments.

DETAILED DESCRIPTION OF THE DRAWINGS

FIG. 1 illustrates oxidation according to the TBARS assay (μmol malondialdehydes (MDA)/kg sample) during formation of the different salmon protein hydrolysates at various turbine/mixing speeds during hydrolysis; SPH-N (normal mixing), SPH-T (turbine mixing) measured as a function of degree of hydrolysis (DH) (%).

FIG. 2 shows a plot of mean scores of odour and taste attributes of SPH-N and SPH-T powder at 20% degree of hydrolysis.

FIG. 3 shows the CACO-2 in vitro cell based increase in iron uptake property for SPH-N and SPH-T at various degrees of hydrolysis.

The process of auto-oxidation and development of rancidity in food is characterized by a free radical chain mechanism proceeding via initiation, propagation, and termination stages.

Initiation: $LH \rightarrow L\cdot$
Propagation: $L\cdot + O_2 \rightarrow LOO\cdot$
$LOO\cdot + LH \rightarrow LOOH + L\cdot$
Termination: $LOO\cdot + LOO\cdot \rightarrow$
$LOO\cdot + L\cdot \rightarrow$ non-radical products
$L\cdot + L\cdot? \rightarrow$ Highly unstable free radicals and hydroperoxides are formed that destroy bio-active peptides and small organic vitamins and help to develop off flavors in the resultant protein hydrolysate powders. Most aquatic species are high in polyunsaturated fatty acids and contain pro-oxidants such as hemoglobin and iron. These muscle constituents interact largely during enzymatic hydrolysis processing and the resultant off taste and odor are carried over into the final aquatic protein hydrolysate powder. Thus, the reaction conditions during enzymatic hydrolysis have been shown to demonstrate a major impact on oxidation. The culprit compounds, such as ketones, aldehydes and alcohols are formed at a steady rate during enzymatic hydrolysis due to the ideal conditions of slightly acid pH, 60° C. temperature and aqueous medium. They then bind to proteins and peptides and form insoluble lipid-protein complexes which leads to the off taste and odor.

In order to measure the progress of oxidation as a variant during various mixing techniques, it was necessary to follow the transformation and/or formation of reactants, intermediates and products. Since many of these compounds are very unstable, and since they are differently affected by the presence of oxygen, pro-oxidants and antioxidants, we used the universal TBARS method to measure oxidation in all its forms. TBARS has been found to be a very good indicator of lipid oxidation in seafood products and is often well correlated with sensory tests. As can be seen from FIG. 1, the turbine mixing of fish byproducts results in significantly less oxidation for the same degree of hydrolyzed protein hydrolysate. This can be attributed to both the higher rate of enzymatic hydrolysis for the turbine mixing system (as shown below in example 1) as well as the lack of pulling into solution of head space gases particularly oxygen and oxidatively produced volatile free radicals which occurs significantly during normal mixing and which is very minimized in turbine mixing. The dissolved oxygen and oxidatively produced free radicals increase the rate of oxidation of the fish protein hydrolysate product in solution for normal mixed protein hydrolysate powder (SPH-N) versus turbine mixed protein hydrolysate powder (SPH-T).

The reduction in TBARS value leads to an improvement in organoleptic profile as shown in FIG. 2. Several taste and odour profiles were measured during the test which was scored from 0 to 100. Rancid fish odor and taste and fishy, sour and bitter taste profiles improved significantly for turbine mixed (SPH-T) versus normal mixed (SPH-N) comparably hydrolyzed protein powder.

Finally, the turbine mixed protein hydrolysate powder also exhibited improved bio-activity as measured by an in vitro CACO-2 cell assay for measuring iron uptake. As can be seen in FIG. 3, the turbine mixed protein hydrolysate powder (SPH-T) has significantly better iron uptake ability as compared to the normal mixed protein hydrolysate powder (SPH-N).

The features of the invention mentioned above as well as others, will emerge more clearly from a reading of the following description of an example embodiment, the said examples being intended to be illustrative and non-limiting.

EXAMPLES

Example 1

The Effect of Turbine Mixing Versus Normal Agitation on Oxidation Levels (TBARS) in Enzyme Hydrolyzed Salmon Protein Hydrolysate Powder Salmon backbones and heads separated and ground after filleting of whole salmon, are subjected to protein hydrolysis using a papain protease extract. The only variable in the experimentation is the method of mixing employed—turbine versus normal agitation using a stirring rod and paddle agitator.

1 kg of salmon backbone and head is ground into smaller pieces using a Waring blender such that the resultant pieces are between 5 mm and 4 cm in size. 100 g of this material is added into a 1 liter jacketed glass reactor and 200 ml of warm water at 60° C. is added. The resultant mass is warmed back to 60° C. using hot water in the jacket. For production of the Normal agitated protein hydrolysate powder (SPH-N), the reactor is equipped with a stirring rod attached to a motor at the top end and a 4 paddle stirrer at the bottom end, ½ inch (1.27 cm) from the bottom of the reactor. For production of the Turbine agitated protein hydrolysate powder (SPH-T), the reactor is equipped with a turbine mixer which is either entirely or partially from the side or the top of the reactor, immersed in the reaction mixture.

Agitation is started and maintained at 50 RPM for the normal agitator and at full vortex speed for the turbine agitator and 1 g of the papain protease extract is added into the reactor. The reaction is stirred and approximately 10 ml of material is extracted from the reactor at designated times and centrifuged at 6000 RPM to separate the mass into solid, water and oil layers. The water layer was extracted with a pipette and dried to a powder in a lyophilizer and the degree of hydrolysis versus TBARS values were determined using methods well described in the art, at different degrees of hydrolysis and plotted as shown in FIG. 1.

Table 1 below also shows a direct comparison of time versus degree of hydrolysis for SPH-N and SPH-T revealing the much quicker hydrolysis time for turbine mixed hydrolysis reactions.

TABLE 1

Time vs. Degree of Hydrolysis for SPH-N and SPH-T

| Time | % DH - SPH-N | % DH SPH-T |
|---|---|---|
| 5 minutes | 4 | 9 |
| 10 minutes | 7 | 17 |
| 15 minutes | 12 | 26 |
| 20 minutes | 17 | 31 |
| 25 minutes | 23 | 38 |

Example 2

The Effect of Turbine Mixing Versus Normal Agitation on Organoleptic Performance in Enzyme Hydrolyzed Salmon Protein Hydrolysate Powder The lyophilized dried salmon protein hydrolysate powders from both mixing methods SPH-N and SPH-T were analyzed by a panel of experts for organoleptic properties against six descriptors on a rising scale of 10-100 used by the marine industry for its products and the results plotted in FIG. 2.

Example 3

The Effect of Turbine Mixing Versus Normal Agitation on Bioactivity Performance as Measured by CACO-2 Cell Uptake Levels by Enzyme Hydrolyzed Salmon Protein Hydrolysate Powder Intestinal cell cultures, like Caco-2 cell lines have gained in popularity as an in-vitro model of iron absorption. The human colon carcinoma cell line, Caco-2, is grown on microporous membranes in bifurcated chambers and the cells differentiated spontaneously into bipolar enterocytes that exhibit many of the characteristics of normal epithelial cells. (microvilli, tight inter-cellular junctions and border associated enzymes). The cells grow differentiated so that the apical pole extends into the upper chamber and the basal lateral pole is exposed to the lower chamber. The study can then measure iron uptake from the apical chamber, transport into the cell and secretion into the basal chamber. These cells have iron transport kinetics supporting both a saturable and non-saturable iron transport pathway, similar to observations in human and animal intestines. It should be noted that only the extrinsic added iron (10 μmol/L) was used to measure the iron uptake in this experiment since no accurate way is available to determine intrinsic iron uptake and hence the values shown represent the minimum uptake that would have occurred in each digest which is a similar assumption as made in human studies.

A modified form of the commercially available 24× well Caco-2 assay kit from Celsis In vitro Technologies was used in this assay. The Celsis kit was pre-plated with Caco-2 cells with Corning Transwell® filters. These Caco-2 cultures are considered acceptable for transport studies and meet the transepithelial electrical resistance (TEER) criteria of 1000 ohms. Uptake of iron was studied with Caco-2 cells grown on permeable membrane supports for 16 days, by which time cells are fully differentiated. At time zero, 1.5 ml of the different protein solutions (1%-32%) and $^{59}$Fe (10 μmol/L) were added to the apical chambers of the inserts. The plates were covered and incubated at 37° C. in a shaking water bath for 120 minutes. To evaluate uptake of 59Fe by the different protein solutions (1%-32%), the membranes were removed, gently washed with PBS and placed in the scintillation vials. Five ml of liquid scintillation cocktail was added to each scintillation vial and radioactive counts were measured on a Beckman LS 6500 multipurpose liquid scintillation counter. Uptake of iron by cell monolayers was expressed as nmol/well. Three wells were examined per treatment and experiments were repeated three times to give n=9 wells per treatment.

Table 2 and FIG. 3 show the results of CACO-2 iron uptake for SPH-N and SPH-T powder at various degree of hydrolysis powders.

TABLE 2

CACO-2 Iron Uptake Values for SPH-N and SPH-T

| % DH | Iron uptake (nmol/cell) SPH-N | Iron uptake (nmol/cell) SPH-T |
|---|---|---|
| 0 | 0.021 | 0.019 |
| 4 | 0.035 | 0.041 |
| 8 | 0.055 | 0.073 |
| 15 | 0.136 | 0.155 |
| 26 | 0.139 | 0.167 |

The invention claimed is:

1. A process for producing an aquatic protein hydrolysate, comprising:
    a) subjecting an aquatic protein source material, water and at least one enzyme to turbine mixing with an axial flow pattern to enzymatically hydrolyze the aquatic protein source material;
    b) stopping the enzymatic hydrolysis by deactivating the at least one enzyme under turbine mixing with the axial flow pattern to obtain a hydrolyzed aquatic peptide fraction and solid material; and
    c) separating the hydrolyzed aquatic peptide fraction from the solid material to obtain the aquatic protein hydrolysate.

2. The process of claim 1, wherein the turbine mixing takes place in a turbine mixing system incorporated into a reactor from the side or the top.

3. The process of claim 1, wherein the at least one enzyme comprises proteases from bacterial, fungal or marine species.

4. The process of claim 1, wherein the aquatic protein source material comprises fish material, aquatic mammals, crustaceans, or mollusks, or any combination of the foregoing.

5. The process of claim 1, further comprising grinding or mincing the aquatic protein source material in the presence of water to produce ground or minced pulp, and utilizing the ground or minced pulp in the enzymatic hydrolysis.

6. The process of claim 5,
    wherein the protein content of the aquatic protein source material in water prior to enzymatic hydrolysis is in the range of 0.1% to 30% w/v of protein/water;
    wherein enzymatic hydrolysis is performed at a pH in the range of 5 to 9;

wherein enzymatic hydrolysis is performed at a temperature in the range of 30° C. to 80° C. at which the at least one enzyme does not become heat inactivated; and wherein enzymatic hydrolysis proceeds for a period in the range from about 10 minutes to 1 hour or until the degree of hydrolysis (% DH) has reached a desired value in the range of 2% to 70% DH.

7. The process of claim 1, wherein the hydrolyzed aquatic peptide fraction is separated from the solid material by concentrating and collecting the hydrolyzed aquatic peptide fraction.

8. The process of claim 7, further comprising drying the separated hydrolyzed aquatic peptide fraction.

9. The process of claim 1, wherein the enzyme is deactivated at a temperature
not below 60° C., for 5 to 60 minutes, followed by cooling.

10. The process according to claim 1, wherein the degree of enzymatic hydrolysis is followed or measured in the aquatic protein hydrolysate.

11. The process according to claim 1, wherein the hydrolyzed aquatic peptide fraction is separated from the solid material by filtration.

12. The process according to claim 11, wherein the filtration is performed using an ultra filtration membrane.

13. The process according to claim 1, wherein the hydrolyzed aquatic peptide fraction is separated from the solid material by centrifugation.

14. The process according to claim 1, further comprising concentrating the separated hydrolyzed aquatic peptide fraction to obtain the aquatic protein hydrolysate.

15. The process according to claim 1, further comprising drying the separated hydrolyzed aquatic peptide fraction to obtain the aquatic protein hydrolysate.

16. The process of claim 1, wherein the aquatic protein source material comprises fish muscle, fish skin, fish viscera, fish bones, fish heads, other fish byproducts, or any combination thereof.

17. The process of claim 4, wherein the crustaceans is whole crustaceans, crustacean meat, crustacean shells, crustacean byproducts, or any combination thereof.

18. The process of claim 1, wherein the at least one enzyme is deactivated at a pH below about 5 or above about 9.

19. The process of claim 12, wherein the ultrafiltration membrane has a molecular weight cut-off between 1 kDa and 30 kDa.

20. The process of claim 13, wherein centrifugation is performed at a speed between 500 and 10000 G.

21. The process of claim 1, wherein the at least one enzyme is a mixture of endo and exo proteases.

22. The process of claim 21, wherein the at least one enzyme is a mixture of endo and exo proteases from Bacillus strains.

23. The process of claim 21, wherein the at least one enzyme is a mixture of endo and exo proteases from Bacillus licheniformis.

24. The process of claim 3, wherein the at least one enzyme is Subtilisin.

* * * * *